US012680138B2

(12) United States Patent     (10) Patent No.:   US 12,680,138 B2

Meltzer     (45) Date of Patent:     Jul. 14, 2026

(54) SPATIAL TRANSCRIPTOMICS IN PIPS

(71) Applicant: ILLUMINA, INC., San Diego, CA (US)

(72) Inventor: Robert Meltzer, Belmont, MA (US)

(73) Assignee: Illumina, Inc., San Diego, CA (US)

( * ) Notice: Subject to any disclaimer, the term of this patent is extended or adjusted under 35 U.S.C. 154(b) by 1079 days.

(21) Appl. No.: 17/825,437

(22) Filed: May 26, 2022

(65) Prior Publication Data

US 2022/0380856 A1     Dec. 1, 2022

Related U.S. Application Data

(60) Provisional application No. 63/194,356, filed on May 28, 2021.

(51) Int. Cl.

| | |
|---|---|
| *C12Q 1/6886* | (2018.01) |
| *C12N 15/10* | (2006.01) |
| *C12Q 1/6841* | (2018.01) |

(52) U.S. Cl.

CPC ....... *C12Q 1/6886* (2013.01); *C12N 15/1065* (2013.01); *C12N 15/1096* (2013.01); *C12Q 1/6841* (2013.01); *C12Q 2600/156* (2013.01); *C12Q 2600/158* (2013.01)

(58) Field of Classification Search

CPC ............ C12N 15/1065; C12N 15/1096; C12Q 1/6841; C12Q 1/6886; C12Q 2600/156; C12Q 2600/158; C12Q 2521/107; C12Q 2535/122; C12Q 2563/179; C12Q 2565/514

See application file for complete search history.

(56) References Cited

U.S. PATENT DOCUMENTS

| | | | |
|---|---|---|---|
| 4,701,415 | A | 10/1987 | Dutton |
| 5,512,439 | A | 4/1996 | Hornes et al. |
| 5,813,759 | A | 9/1998 | Gebrian |
| 6,210,891 | B1 | 4/2001 | Nyren et al. |
| 6,306,597 | B1 | 10/2001 | Macevicz |
| 6,309,833 | B1 | 10/2001 | Edman et al. |
| 6,828,100 | B1 | 12/2004 | Ronaghi |
| 6,833,246 | B2 | 12/2004 | Balasubramanian |
| 6,911,345 | B2 | 6/2005 | Quake et al. |
| 7,232,656 | B2 | 6/2007 | Balasubramanian et al. |
| 7,537,897 | B2 | 5/2009 | Brenner et al. |
| 7,598,035 | B2 | 10/2009 | Macevicz |
| 7,835,871 | B2 | 11/2010 | Kain et al. |
| 7,842,457 | B2 | 11/2010 | Berka et al. |
| 7,960,120 | B2 | 6/2011 | Rigatti et al. |
| 8,012,690 | B2 | 9/2011 | Berka et al. |
| 8,629,323 | B2 | 1/2014 | Weeks |
| 8,715,934 | B2 | 5/2014 | Diehl et al. |
| 8,748,102 | B2 | 6/2014 | Berka et al. |
| 8,765,380 | B2 | 7/2014 | Berka et al. |
| 9,011,777 | B2 | 4/2015 | Beer |
| 9,012,390 | B2 | 4/2015 | Holtze et al. |
| 9,085,798 | B2 | 7/2015 | Chee |
| 9,260,751 | B2 | 2/2016 | Diehl et al. |
| 9,388,465 | B2 | 7/2016 | Hindson et al. |
| 9,399,797 | B2 | 7/2016 | Hutchison et al. |
| 9,562,837 | B2 | 2/2017 | Link |
| 9,567,645 | B2 | 2/2017 | Fan et al. |
| 9,567,646 | B2 | 2/2017 | Fan et al. |
| 9,580,736 | B2 | 2/2017 | Tan et al. |
| 9,598,736 | B2 | 3/2017 | Fan et al. |
| 9,637,799 | B2 | 5/2017 | Fan et al. |
| 9,650,629 | B2 | 5/2017 | Froehlich et al. |
| 9,695,474 | B2 | 7/2017 | Johnson et al. |
| 9,701,998 | B2 | 7/2017 | Tindson et al. |
| 9,708,654 | B2 | 7/2017 | Hunicke-Smith et al. |
| 9,783,847 | B2 | 10/2017 | Chee |
| 9,951,386 | B2 | 4/2018 | Hindson et al. |
| 10,030,267 | B2 | 7/2018 | Hindson et al. |
| 10,041,116 | B2 | 8/2018 | Hindson et al. |
| 10,131,958 | B1 | 11/2018 | Fan et al. |
| 10,151,003 | B2 | 12/2018 | Fan et al. |
| 10,155,981 | B2 | 12/2018 | Brenner et al. |
| 10,202,628 | B2 | 2/2019 | Church et al. |
| 10,208,356 | B1 | 2/2019 | Fan et al. |
| 10,221,442 | B2 | 3/2019 | Hindson et al. |
| 10,240,192 | B2 | 3/2019 | Berka et al. |

(Continued)

FOREIGN PATENT DOCUMENTS

| | | | |
|---|---|---|---|
| AU | 2013203624 | A1 | 5/2013 |
| EP | 3819637 | A1 | 5/2021 |

(Continued)

OTHER PUBLICATIONS

International Search Report and Written Opinion issued in International Application No. PCT/US2022/031061, date of mailing: Aug. 16, 2022, 8 pages.

Karlsson, 2016, Counting Molecules in cell-free DNA and single cells RNA, Thesis, Division of Molecular Neurobiology Department of Medical Biochemistry and Biophysics, Karolinska Institutet, 51 pages.

Kukurba, 2015, RNA Sequencing and Analysis, Cold Spring Harb Protoc 11:951-969.

Quail, 2012, A tale of three next generation sequencing platforms: comparison of Ion Torrent, Pacific Biosciences and Illumina MiSeq sequencers, BMC Genomics 13:341, 13 pages.

(Continued)

*Primary Examiner* — Jeremy C Flinders

(74) *Attorney, Agent, or Firm* — Illumina, Inc.

(57) ABSTRACT

This disclosure provides methods and systems for single-cell, multi-omic analysis of target cells without microfluidic devices. The disclosed methods involve the use of template particles to template the formation of monodisperse droplets to generally capture a single target cell from a population of cells in an encapsulation, derive a plurality of distinct mRNA molecules from the single target cell, and quantify the distinct mRNA molecules to generate an expression profile. Nucleic-acid-tagged antibody conjugates are used for simultaneous proteomic analysis along with the gene expression profiling.

21 Claims, 4 Drawing Sheets

(56)                References Cited

U.S. PATENT DOCUMENTS

| | | | |
|---|---|---|---|
| 10,240,197 | B1 | 3/2019 | Brenner et al. |
| 10,253,375 | B1 | 4/2019 | Fan et al. |
| 10,266,883 | B2 | 4/2019 | Chee |
| 10,280,459 | B1 | 5/2019 | Brenner et al. |
| 10,285,940 | B2 | 5/2019 | Mason et al. |
| 10,329,557 | B2 | 6/2019 | Johnson et al. |
| 10,344,329 | B2 | 7/2019 | Hindson et al. |
| 10,392,662 | B1 | 8/2019 | Brenner et al. |
| 10,400,280 | B2 | 9/2019 | Hindson et al. |
| 10,415,030 | B2 | 9/2019 | Marshall et al. |
| 10,457,986 | B2 | 10/2019 | Hindson et al. |
| 10,501,793 | B2 | 12/2019 | Chee |
| 10,584,381 | B2 | 3/2020 | Hindson et al. |
| 11,008,607 | B2 | 5/2021 | Chee |
| 11,060,149 | B2 | 7/2021 | Steelman |
| 11,104,961 | B2 | 8/2021 | Fontanez et al. |
| 11,142,791 | B2 | 10/2021 | Abate et al. |
| 11,549,138 | B2 | 1/2023 | Chee |
| 11,692,214 | B2 | 7/2023 | Nolan |
| 11,932,902 | B2 | 3/2024 | Nolan |
| 12,234,505 | B2 | 2/2025 | Chee |
| 12,275,993 | B2 | 4/2025 | Ziraldo et al. |
| 12,297,487 | B2 | 5/2025 | Chee |
| 12,305,239 | B2 | 5/2025 | Ziraldo et al. |
| 12,416,102 | B2 | 9/2025 | Ziraldo et al. |
| 2002/0132251 | A1 | 9/2002 | Shuber |
| 2003/0143599 | A1 | 7/2003 | Makarov et al. |
| 2003/0180737 | A1 | 9/2003 | Gu et al. |
| 2004/0005585 | A1 | 1/2004 | Bi et al. |
| 2006/0024681 | A1 | 2/2006 | Smith et al. |
| 2006/0177836 | A1 | 8/2006 | McKernan et al. |
| 2006/0292611 | A1 | 12/2006 | Berka et al. |
| 2007/0080316 | A1 | 4/2007 | Sauer et al. |
| 2007/0114362 | A1 | 5/2007 | Feng et al. |
| 2008/0004436 | A1 | 1/2008 | Tawfik |
| 2009/0280475 | A1 | 11/2009 | Pollack et al. |
| 2011/0009278 | A1 | 1/2011 | Kain et al. |
| 2011/0086780 | A1 | 4/2011 | Colston, Jr. et al. |
| 2011/0118151 | A1 | 5/2011 | Eshoo et al. |
| 2011/0311978 | A1 | 12/2011 | Makarewicz, Jr. et al. |
| 2012/0295269 | A1 | 11/2012 | Pourahmadi et al. |
| 2012/0316074 | A1 | 12/2012 | Saxonov |
| 2013/0115169 | A1 | 5/2013 | Ahann et al. |
| 2014/0155295 | A1 | 6/2014 | Hindson et al. |
| 2015/0133312 | A1 | 5/2015 | Bielas et al. |
| 2015/0225777 | A1 | 8/2015 | Hindson et al. |
| 2016/0186267 | A1 | 6/2016 | So et al. |
| 2016/0250608 | A1 | 9/2016 | Anders et al. |
| 2016/0274103 | A1 | 9/2016 | Piloto et al. |
| 2017/0192030 | A1 | 7/2017 | Lapham et al. |
| 2017/0218437 | A1 | 8/2017 | Seul et al. |
| 2017/0232417 | A1 | 8/2017 | Ebofsky et al. |
| 2017/0255160 | A1 | 9/2017 | Numata et al. |
| 2018/0010105 | A1 | 1/2018 | Rogers et al. |
| 2018/0051321 | A1 | 2/2018 | Hindson et al. |
| 2018/0119216 | A1 | 5/2018 | Jamshidi et al. |
| 2018/0133715 | A1 | 5/2018 | Craig et al. |
| 2018/0179553 | A1 | 6/2018 | Watson et al. |
| 2018/0216162 | A1 | 8/2018 | Belhocine et al. |
| 2018/0237836 | A1 | 8/2018 | Abate et al. |
| 2018/0274027 | A1 | 9/2018 | Hindson et al. |
| 2018/0355407 | A1 | 12/2018 | Utharala et al. |
| 2019/0085412 | A1 | 3/2019 | Fan et al. |
| 2019/0153532 | A1 | 5/2019 | Bharadwaj et al. |
| 2019/0153550 | A1 | 5/2019 | Steinmetzer et al. |
| 2019/0177789 | A1 | 6/2019 | Hindson et al. |
| 2019/0323003 | A1 | 10/2019 | Ramji et al. |
| 2019/0323091 | A1 | 10/2019 | Bramlett et al. |
| 2019/0352714 | A1 | 11/2019 | Salk et al. |
| 2019/0381497 | A1 | 12/2019 | DiCarlo et al. |
| 2019/0382753 | A1 | 12/2019 | Steemers et al. |
| 2020/0040385 | A1 | 2/2020 | Beechem et al. |
| 2020/0080112 | A1 | 3/2020 | Zhang et al. |
| 2020/0190513 | A1 | 6/2020 | Fernandez et al. |
| 2020/0261879 | A1 | 8/2020 | Abate et al. |
| 2020/0324287 | A1 | 10/2020 | Vijayan et al. |
| 2020/0376488 | A1 | 12/2020 | Wu et al. |
| 2021/0010070 | A1 | 1/2021 | Schnall-Levin et al. |
| 2021/0054369 | A1 | 2/2021 | Meltzer et al. |
| 2021/0214721 | A1 | 7/2021 | Fontanez et al. |
| 2021/0214763 | A1 | 7/2021 | Fontanez et al. |
| 2021/0214769 | A1 | 7/2021 | Fontanez et al. |
| 2021/0214792 | A1 | 7/2021 | Fontanez et al. |
| 2021/0214802 | A1 | 7/2021 | Fontanez et al. |
| 2021/0215591 | A1 | 7/2021 | Fontanez et al. |
| 2021/0301354 | A1 | 9/2021 | Kiani |
| 2021/0332432 | A1 | 10/2021 | Kiani |
| 2021/0340596 | A1 | 11/2021 | Meltzer et al. |
| 2021/0381064 | A1 | 12/2021 | Fontanez et al. |
| 2022/0017892 | A1 | 1/2022 | Meltzer et al. |
| 2022/0135966 | A1 | 5/2022 | Meltzer |
| 2022/0136071 | A1 | 5/2022 | Meltzer |
| 2022/0154248 | A1 | 5/2022 | Abate et al. |
| 2022/0235416 | A1 | 7/2022 | Fontanez et al. |
| 2022/0267761 | A1 | 8/2022 | Fontanez et al. |

FOREIGN PATENT DOCUMENTS

| | | | |
|---|---|---|---|
| JP | 2021072863 | A | 5/2021 |
| WO | 1997/008547 | A1 | 3/1997 |
| WO | 2010/117620 | A2 | 10/2010 |
| WO | 2011/047307 | A1 | 4/2011 |
| WO | 2012/116146 | A1 | 8/2012 |
| WO | 2012/149042 | A2 | 11/2012 |
| WO | 2013/165748 | A1 | 11/2013 |
| WO | 2014/028537 | A1 | 2/2014 |
| WO | 2014/100434 | A1 | 6/2014 |
| WO | 2014/146025 | A1 | 9/2014 |
| WO | 2014/153071 | A1 | 9/2014 |
| WO | 2015/157369 | A1 | 10/2015 |
| WO | 2015/187792 | A1 | 12/2015 |
| WO | 2016/025815 | A1 | 2/2016 |
| WO | 2016/040476 | A1 | 3/2016 |
| WO | 2016/126871 | A2 | 8/2016 |
| WO | 2016/138080 | A1 | 9/2016 |
| WO | 2016/172373 | A1 | 10/2016 |
| WO | 2017/161306 | A1 | 9/2017 |
| WO | 2019/011971 | A1 | 1/2019 |
| WO | 2019/023627 | A1 | 1/2019 |
| WO | 2019/139650 | A2 | 7/2019 |
| WO | 2019/157529 | A1 | 8/2019 |
| WO | 2019/204229 | A1 | 10/2019 |
| WO | 2019/217552 | A1 | 11/2019 |
| WO | 2019/222523 | A2 | 11/2019 |
| WO | 2020/037214 | A1 | 2/2020 |
| WO | 2020/069268 | A1 | 4/2020 |
| WO | 2020/069298 | A1 | 4/2020 |

OTHER PUBLICATIONS

Stoeckius, 2017, Large-scale simultaneous measurements of epitopes and transcriptomes in single cells, Nat Methods 14(9):865-868.

Berensmeier, 2006, Magnetic particles for the separation and purification of necleic acids, Applied Microbiology and Biotechnology, 73:495-504.

Biocompare, 2013, How to maintain a constant temp in your CO2 incubator, Jan. 17, 2013 (Jan. 17, 2013) [online] retrieved from <URL: https://www.biocompare.com/Editorial-Articles/126328-Incubators/#:~text=A jacket of water circulates, thermal buffer against outside air.> entire document, 7 pages.

Bowman, 2013, Multiplexed Illumina sequencing libraries from picogram quantities of DNA, BMC Genomics 14:466 (8 pages).

Brouzes, 2009, Droplet microfluidic technology for single-cell high-throughput screening, Proc Natl Acad Sci 106 (34):14195-14200.

Cai, 2019, Selection of DNA-encoded libraries to protein targets within and on living cells, Journal of the American Chemical Society, 141(43):1-11.

Cheng, 2020, Ultra-senstive and rapid detection of nucleic acids and microorganisms in body fluids using single molecule tethering, Nature Communications, 11(1):1-9.

(56)  References Cited

OTHER PUBLICATIONS

Datlinger, 2017, Pooled CRISPR screening with single-cell transcriptome readout, Nature Methods 4(3):297-301.
Eastbum, 2013, Ultrahigh-trhoughput mammalian single-cell reverse-transcriptase polymerase chain reaction in microfluidic drops, Anal Chem 85:8016-8021.
Fan, 2017, Barcode Doublets, JEFWorksLab (5 pages).
Figueiredo, 2007, Cost effective method for construction of high quality cDNA libraries, Biomol Eng 24:419-421.
Fu, 2015, Uniform and accurate single-cell sequencing based on emulsion whole-genome amplification, PNAS 112(38):11923-11928.
Hatori, 2019, Particle-Templated Emulsification for Microfluidics-Free Digital Biology, Analytical Chemistry, 90:9813-9820.
High containment laboratories at CDC—Fifty Years of Excellence, Centers for Disease Control and Prevention, retreived from the internet, <https://www.cdc.gov/ncezid/dhcpp/hcl-50/high-containment-laboratories.html>, 1 page.
Jacobsen, 2004, Direct isolation of poly(A)+ RNA from 4 M guanidine thiocyanate-lysed cell extracts using locked nucleic acid-oligo(T) capture, Nucleic Acids Research, 32(7), 10 pages.
Kim, 2018, Single-Cell RT-PCR in Microfluidic Droplets with Integrated Chemical Lysis, Anal Chem 90(2):1273-1279.
Klein, 2015, Droplet barcoding for single cell transcriptomics applied to embryonic stem cells, Cells, 161(5):1187-1201.
Kumaresan, 2008, High-throughput single copy DNA amplification and cell analysis in engineered nanoliter droplets, Anal Chem, 80:3522-3529.
Kumari, 2017, Quantification of Circulating Free DNA as a Diagnostic Marker in Gall Bladder Cancer, Pathology & Oncology Research, 23:91-97.
Lage, 2003, Whole genome analysis of genetic alterations in small DNA samples using hyperbranched strand displacement amplification and array-CGH, Genome Res 13:294-307.

Lyons, 2017, Large-scale DNA barcode library generation for biomolecule identification in high-throughput screens, Sci Rep 7:13899 (7 pages).
Markus, 2021, Analysis of recurrently protected genomic regions in cell-free DNA found in urine, Science Translational Medicine, 13(581):1-31.
Mazutis, 2013, Singl-cell analysis and sorting using droplet-based microfluidics, Nature Protocols, 8(5):870-891.
Nishikawa, 2015, Monodisperse picoliter droplets for low-bias and contamination-free reactions in single-cell whole genome amplification, PLoSOne 10(9):e0138733 (15 pages).
Patel, 2019, Design and fabrication of low cost vortex mixer using additive manufacturing, International Journal of Applied Engineering Research 14(1):246-249.
Petersen, 2021, Screening of DNA-encoded small molecule libraries inside a living cell, Journal of the American Chemical Society, 143(7):2751-2756.
Replogle, 2020, Combinatorial single-cell CRISPR screens by direct guide RNA capture and targeted sequencing, Nat. Biotechnol. 38(8):954-961.
Roche, 2011, emPCR amplification method manual, 454 Life Sciences Corp (12 pages).
Sidore, 2016, Enhanced sequencing coverage with digital droplet multiple displacement amplification, Nucl Acids Res 44(7):e66 (9 pages).
Stoeckius, 2017, Simultaneous epitope and transcriptome measurment in single cells, Nat Meth online pub (10 pages).
Tamminen, 2015, Single gene-based distinction of individual microbial genomes from a mixed population of microbial cells Front Microb 6:195 (10 pages).
Vitale, 2019, An optimized workflow to evaluate estrogen receptor gene mutations in small amounts of cell-fee DNA, The Journal of Molecular Diagnostics, 21(1):123-127.
Walls, 2020, Structure, Function, and Antigenicity of the SARS-CoV-2 Spike Glcoprotein, Cell, 181(2):281-292.
Zilionis, 2016, Single-cell barcoding and sequencing using droplet microfluidics, Natutre Prot 12(1):44-73.

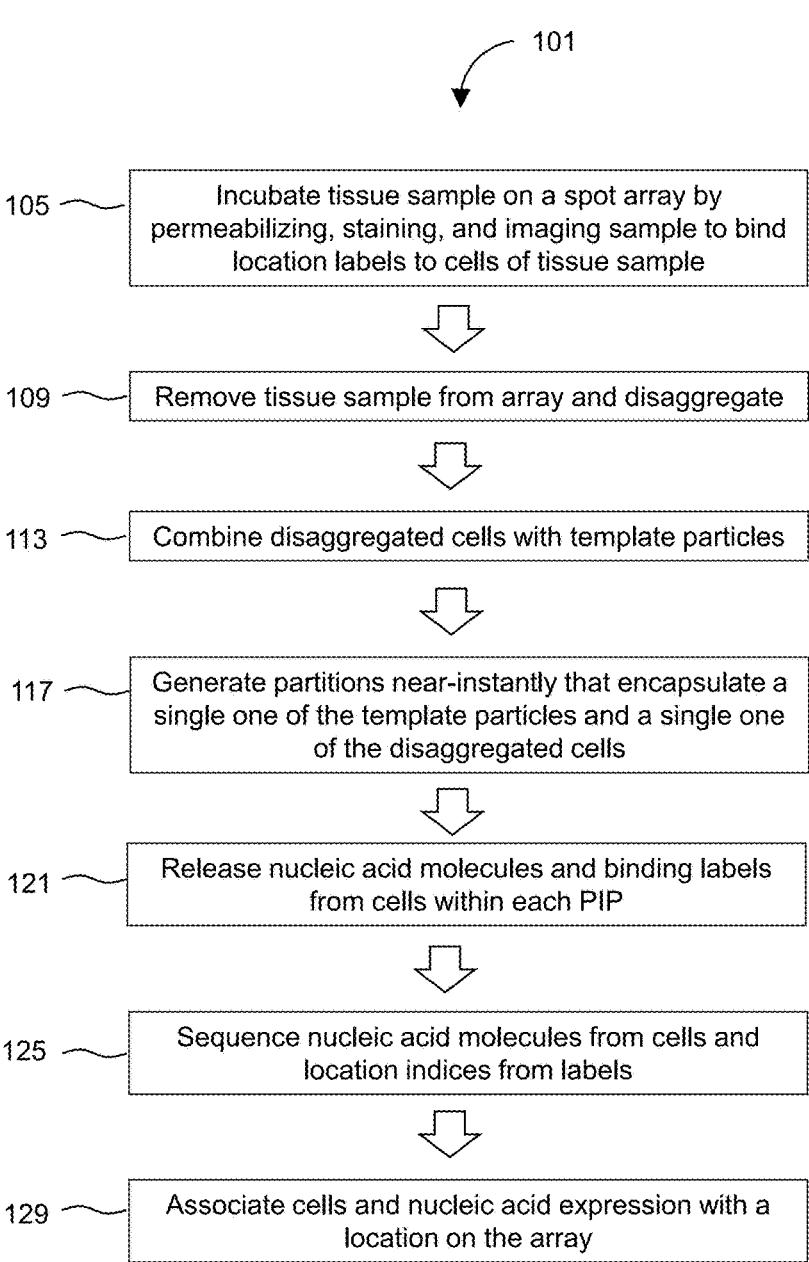

101

105 — Incubate tissue sample on a spot array by permeabilizing, staining, and imaging sample to bind location labels to cells of tissue sample 109 — Remove tissue sample from array and disaggregate 113 — Combine disaggregated cells with template particles 117 — Generate partitions near-instantly that encapsulate a single one of the template particles and a single one of the disaggregated cells 121 — Release nucleic acid molecules and binding labels from cells within each PIP 125 — Sequence nucleic acid molecules from cells and location indices from labels 129 — Associate cells and nucleic acid expression with a location on the array

FIG. 1

Gene profile 1        Gene profile 2        Gene profile 3

SPATIAL TRANSCRIPTOMICS IN PIPS

TECHNICAL FIELD

The invention generally relates to the field of spatial transcriptomics.

BACKGROUND

Cancer is the second leading cause of death globally,
responsible for nearly ten million deaths every year. Cancer
is a genetic disease, caused by hereditary or acquired muta-
tions in genetic information stored in DNA that control how
cells grow and divide. There are many different kinds of
mutations in DNA that have been linked with cancers, but
generally each individual cancer patient's profile of genetic
mutations is different. Moreover, the genetic information
stored in DNA must first be transcribed into messenger RNA
(mRNA) before being expressed in a cell. The degree to
which genetic information in DNA is actually expressed into
mRNA is also unique to each individual and each given cell.
That is to say, even if a patient can be identified as having
a DNA mutation associated with cancer, it would remain
unknown whether, to what degree, and what cells in the
subject are expressing a cancer phenotype.
Single-cell sequencing of RNA has revolutionized the
detection of cancer cell expression in patients by providing
scientists with the actual expression levels of genes associ-
ated with cancers in cells from the complex mixtures from
which they are prepared. Popular methods for isolating
single cells and their RNA expression employ flow cytom-
etry and droplet microfluidics to separate single cells one at
a time. These methods, however, require complicated equip-
ment that is both expensive and difficult to use. Moreover,
because each cell must be processed individually, such
methods are rate limited and require extensive periods of
time (often days) to separate cancer cells from surrounding
cells.
Additionally, because popular methods for cell expression
profiling require disaggregated cells from their surrounding
tissue, the location of where cells expressing a cancer
phenotype spatially within a tissue is lost. As a result, the
location and boundaries of tumors or other complex cellular
topologies cannot be derived prior to the emergence of a
visual lesion and biopsy. This has resulted in early detection
of cancer gene expression being unaffordable and unavail-
able to the majority of cancer patients.

SUMMARY

This invention provides methods for single cell gene
expression analysis that pair gene expression profiles for
cells with the spatial location of those cells in relation to the
tissue from which they were derived. The present invention
provides methods for binding a label to cells that identifies
their location relative to an array, followed by near-instan-
taneously separation of those cells together with their bound
labels into pre-templated instant partitions (PIPs). Nucleic
acid molecules from the cells, including mRNA molecules
and the bound labels, can then be released from cells within
each PIP and provided a barcode unique to that PIP. The
expression profiles for each PIP, and therefore each cell, can
then be paired to the labels released in each PIP to provide
a location on the array for that cell and its expression profile.
For example, a tissue sample can be placed on the array and
incubated with labels present on the array that identify their
coordinates on the array. After utilizing methods of the invention, not only will the gene expression profile for cells
from the tissue sample be known, but also the location of
each cell on the array and therefore the tissue sample.
Additionally, methods of the present invention are per-
formed without the need for complex and expensive machin-
ery as required by microfluidic cell separation techniques,
dramatically reducing the cost of gene expression analysis,
profiling, and spatial transcriptomics in early cancer detec-
tion.
The instant invention describes a method for gene expres-
sion profiling that comprises incubating a tissue sample
comprising a plurality of cells on an array comprising a
plurality of labels with binding specificity for a cell protein
(for example a cell surface or nuclear envelope protein) and
having a nucleic acid index identifying the location of the
label on the array. The tissue may then be disaggregated and
a plurality of cells separated from the tissue sample. The
disaggregated plurality of cells is then combined with tem-
plate particles and a plurality of uniform partitions are
generated near-instantly that encapsulate a single one of the
template particles and a single one of the disaggregated cells
to form pre-templated instant partitions (PIPs). Nucleic acid
molecules and proteins from the disaggregated cells in each
PIP, including proteins bound by a label from the array are
then released within the PIP.
The labels comprise an antibody or fragment thereof or a
lipophilic aptamer. Lipophilic aptamers are described in
Tokunaga, 2013, Systematic exploration of lipophilic tags
that allow efficient anchoring of aptamers to live cell sur-
faces, Chem Lett 42(2):127-129; labeling antibodies, for
example Antibody Derived Tags (ADTs) are described in
Stoeckius, 2017, Large-scale simultaneous measurements of
epitopes and transcriptomes in single cells, Nat Methods
14(9):865-868, the entirety of the contents of each of which
are incorporated herein.
The step of releasing nucleic acid molecules from the
cells may further comprise releasing RNA molecules, for
example RNA transcripts. Each of the nucleic acid mol-
ecules and labels released from a cell in each PIP may be
provided a nucleic acid barcode unique to the PIP. Each of
the nucleic acid molecules may be provided with a unique
molecular barcode. Providing a nucleic acid barcode unique
to the PIP and a unique molecular identifier may comprises
the step of reverse transcribing RNA molecules to form
cDNA complements comprising the unique molecular iden-
tifier and barcode unique to the PIP. Providing a nucleic acid
barcode unique to the PIP to the label make comprise
tagging the nucleic acid index of the nucleic acid barcode.
Methods of the invention may further comprise the step of
sequencing the nucleic acids, including nucleic acids
released from cells and nucleic acid indexes, to generate
sequence reads. For example, methods of the invention may
comprise sequencing cDNA complements to generate
sequence reads associated with RNA molecules from the
cells.
Advantageously, each label from a PIP may be identified
with that PIP, for example by the barcode unique to the PIP
tagged to the label index, and then associated with each of
the sequence reads associated with an RNA molecule from
the same PIP to generate a set of sequence reads for each
label. The index from each label may then be used to assign
a location on the array to the set of sequence reads associated
with the label. Because each PIP has only a single cell and
the indices, the gene expression for each cell can be mapped
to a set of coordinates on the array.
In aspects of the invention, the step of incubating the
tissue sample on the array may comprise: i) permeabilizing the tissue sample; ii) staining the tissue sample; and/or iii) imaging the tissue sample. Permeabilizing the tissue sample is advantageous because the tissue sample, cells, or proteins from cells may become fixed to the array to prevent movement during incubation of the tissue sample on the array. Staining the tissue sample is advantageous because physically distinct regions and cells of the tissue can be made visually distinct. Moreover, staining the tissue sample may be used to release the labels from the array to bind to the plurality of cells. For example, the labels may be spotted onto the array and lyophilized and released upon staining the tissue sample. Imaging the tissue sample is advantageous because the physical location of the tissue sample, for example when permeabilized and/or stained on the array, can be visualized and cross-referenced to the coordinates of the array.

Labels identifying locations on the array may be placed on the array by any conventional method. The array may be a glass array. Labels are spotted onto a glass array. Labels may be lyophilized and released upon wetting of the array.

Indexes may also identify locations on the array by a variety of methods. For example, a single label may identify at least the X and Y coordinates of the label on the array. Alternatively, one label may identify the X coordinate on the array and a second label at the second location may identify the Y location on the array.

Labels may be affixed to the array by any known method. For example, labels may be covalently bonded to the glass array. Labels may be covalently bonded to the glass array by siloxane chemistry. Labels may be covalently bonded to the glass array by their index, and preferably the index may comprise a moiety for controlled release of label.

The present invention is based on the partitioning of cells near-instantly, rather than one by one, into pre-templated instant partitions (PIPs).

Methods of the present invention may simultaneously separate disaggregated single cells by combining the template particles with the disaggregated single cells in a first fluid, adding a second fluid to the first fluid, and agitating the fluids to generate a plurality of pre-templated instant partitions simultaneously that contain a single one of the template particles and a single one of the disaggregated single cells. Simultaneously or near-instantly are used interchangeably and include within seconds, within minutes, or within hours. Simultaneously or near-instantly does not include in serial as envisioned by microfluidic equipment. In aspects of the invention, the step of combining scavenger molecules and template particles with a plurality cells may comprise combining the scavenger molecules, template particles, and plurality of cells in a first fluid and adding a second fluid to the first fluid.

The first fluid and the second fluid may be immiscible. For example, the first fluid may comprise an aqueous phase fluid and/or the second fluid may comprise an oil. The first fluid may comprise reagents selected from, for example, buffers, salts, lytic enzymes (e.g. proteinase k) and/or other lytic reagents (e. g. Triton X-100, Tween-20, IGEPAL, or combinations thereof), nucleic acid synthesis reagents e.g. nucleic acid amplification reagents or reverse transcription mix, or combinations thereof. The second fluid may comprise fluorocarbon oil, a silicone oil, or a hydrocarbon oil, or a combination thereof. Agitating fluids may comprise vortexing, shaking, flicking, stirring, pipetting, or any known method for mixing solutions.

The step of releasing in each PIP nucleic acid molecules from the cells may comprise lysing each of the single cells contained within the PIPs. Releasing nucleic acid molecules or proteins from single cells may comprise lysis of the single cells within the PIPs. Lysis may be induced by a stimulus such as heat, osmotic pressure, lytic reagents (e.g., DTT, beta-mercaptoethanol), detergents (e.g., SDS, Triton X-100, Tween-20), enzymes (e.g., proteinase K), or combinations thereof.

Advantageously, methods of the invention do not require microfluidic equipment or maintaining microfluidic control. For example, the step of combining cells and template particles and the step of generating a plurality of uniform partitions near-instantly may be performed in a tube, for example a centrifuge tube, microcentrifuge tube, or polymerase chain reaction (PCR) tube.

Template particles may comprise any known particles that can be useful for forming PIPs. The template particles may be hydrogels, for example, hydrogels comprising agarose, alginate, a polyethylene glycol (PEG), a polyacrylamide (PAA), acrylate, acrylamide/bisacrylamide copolymer matrix, azide-modified PEG, poly-lysine, polyethyleneimine, and combinations thereof. In certain instances, template particles may be shaped to provide an enhanced affinity for the single cells. For example, the template particles may be generally spherical but the shape may contain features such as flat surfaces, craters, grooves, protrusions, and other irregularities in the spherical shape that promote an association with a single cell such that the shape of the template particle increases the probability of templating a PIP that contains a single cell.

Tubes for single cell analysis of the present invention may be selected based on the volume of sample from which cells need to be separated and/or based on the number of cells to be separated. For example, the tube may be a single large tube, such as a conical centrifuge tube, such as those sold under the trade name FALCON as sold by Corning Inc., Corning, New York, for example a tube with a volume of less than 40 mL. The tubes may also be wells, such as standard 96 sample well kits. The tubes may also be centrifuge, microcentrifuge, or PCR tubes, such as those sold under the trade name EPPENDORF by Eppendorf, Hamburg, Germany. Such tubes, for example, may be between 0.1 and 6 mL.

The step of generating in the tube a plurality of uniform partitions near-instantly that encapsulate a single one of the template particles and a single one of the cells may also comprise generating a plurality of partitions that encapsulate a single one of the template particles and do not encapsulate a cell. For example, where 100,000 template particles are combined with 10,000 single cells in a first fluid, it is expected that generating partitions may result in about 90,000 partitions that encapsulate a single template particle and do not encapsulate a cell. Additionally, in rarer cases, two template particles may be encapsulated by a single partition, or two cells may be encapsulated in a single partition.

BRIEF DESCRIPTION OF DRAWINGS

FIG. 1 diagrams a method for single cell profiling.

DETAILED DESCRIPTION

The present invention provides methods for binding a label to cells that identifies their location relative to an array, followed by near-instantaneously separation of those cells together with their bound labels into pre-templated instant partitions (PIPs). Nucleic acid molecules from the cells, including mRNA molecules and the bound labels, can then be released from cells within each PIP and provided a barcode unique to that PIP. The expression profiles for each PIP, and therefore each cell, can then be paired to the labels released in each PIP to provide a location on the array for that cell and its expression profile. The invention provides methods for improving single cell sequencing to directly link single cell transcriptomics to tissue morphology in histological slices. Upon disaggregation of that tissue, the spatial relations are maintained by the encoded indices, and may be reconstructed computations after next generation sequencing.

FIG. 1 diagrams and aspect of the methods of the invention. A tissue sample, for example a fresh of fixed histological slice, is incubated on a spot array by permeabilizing, staining, and imaging the sample 105. The incubation process, for example through staining, releases labels on the array that bind to cells of the tissue and have a nucleic acid index that identifies their coordinates on the array. The tissue sample is removed from the array and disaggregated to separate the now labeled cells 109. The disaggregated cells are combined with template particles 113 and partitions are generated near-instantly that encapsulate a single one of the template particles and a single one of disaggregated cells 117. Nucleic acid molecules and binding labels are released from cells within each PIP 121. The nucleic acid molecules from cells and location indices from labels are sequences and associated, for example based on a barcode provided to each nucleic acid molecule and label unique to the PIP in which they were released. The cell and its corresponding released and sequenced nucleic acid molecules can then be mapped to a location on the array based on the corresponding index with the same PIP-unique barcode.

Figure 2:
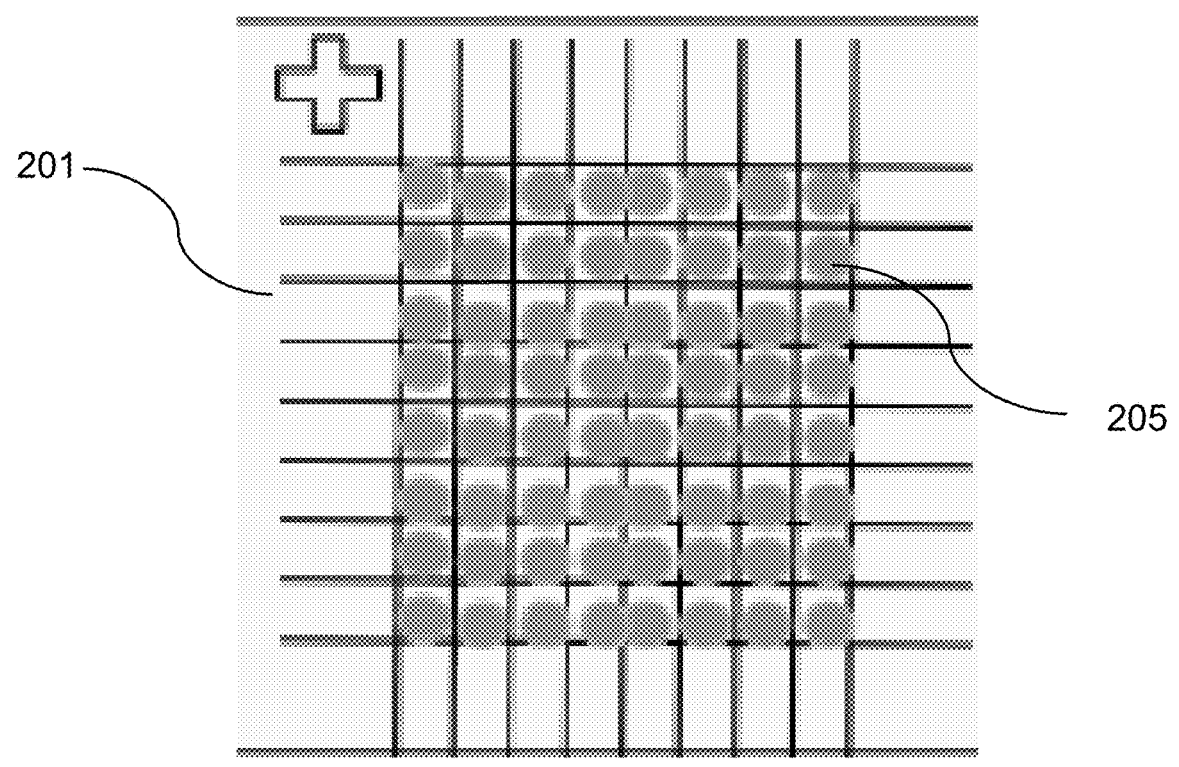
FIG. 2. depicts an array of the invention.

FIG. 2 depicts an array of the invention. The array 201 is a 2D matrix of micro-spotted antibody derived tags (ADTs) 205 to add discrete spatial barcodes to individual cells or nuclei in tissue slices. Advantageously the array may be a slide, for example a microscopy slide. Each spot of ADTs 205 carries an individual barcode index. The array may also comprise lipophilic tags in addition to or as an alternative to antibody derived tags. Each spot 205 may be dried to the slide and the spatial arrangement may be uniform across slides, printed in reference to locating fiducial markers.

Figure 3:
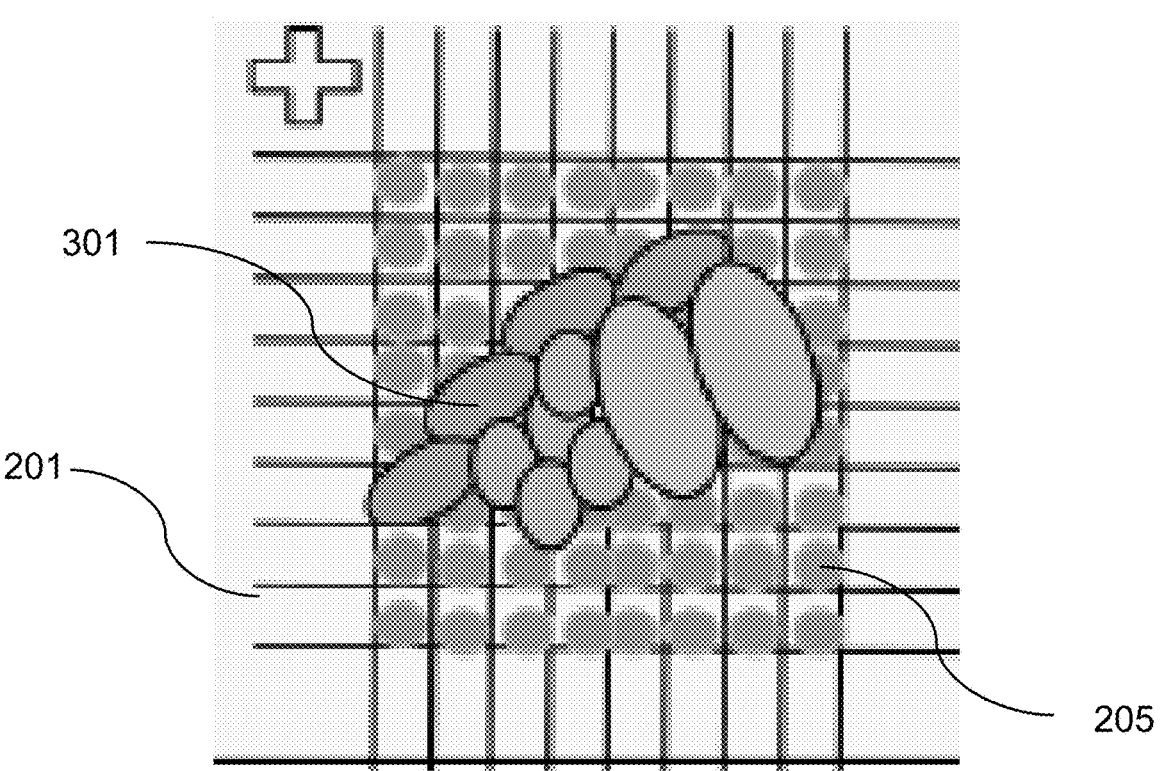
FIG. 3 depicts an array of the invention with tissue placed on the array.

FIG. 3 depicts an array of the invention with a tissue section 301 overlaid on the array 201. The tissue section 301 may be fixed or fresh. The tissue may be permeabilized, stained, and imaged. Cell features may be assigned a spatial index based on grid alignments. Staining of the tissue 301 may release the spotted ADTs which may interact with nuclear envelope epitopes.

Figure 4:
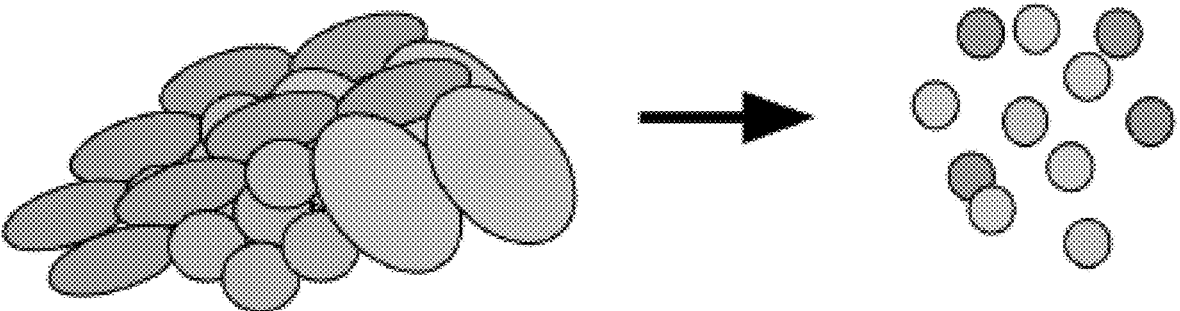
FIG. 4 depicts disaggregation of tissue.

FIG. 4 depicts disaggregated tissue cells. Tissue sections are recovered from the slide, cells disaggregated, and single nuclei suspension recovered. Each nucleus carries the spatial ADT marker from the grid and can be assigned a location of origin from imaging.

Figure 5:
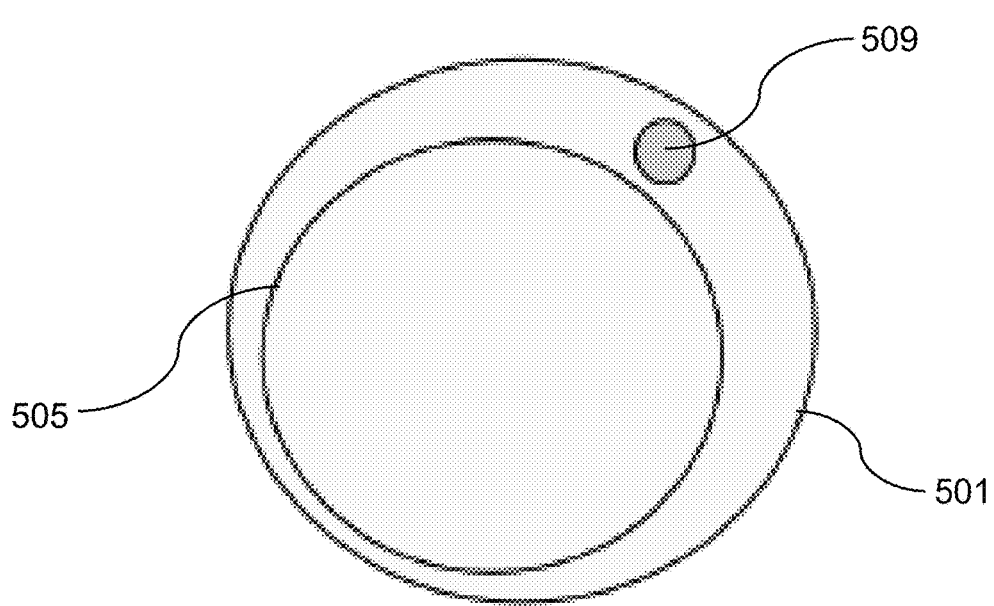
FIG. 5 depicts formation of PIPs with a single cell.

FIG. 5 depicts a PIP of the invention with a disaggregated cell. The disaggregated cells 509 are combined with template particles 505 and PIP emulsions 501 are formed, for example by disrupting the mixture. Spatial tags and nucleic acid molecules are released from cells, captured, and sequenced, allowing spatial information regarding the cell and the nuclear transcriptome to simultaneously be captured.

Figure 6:
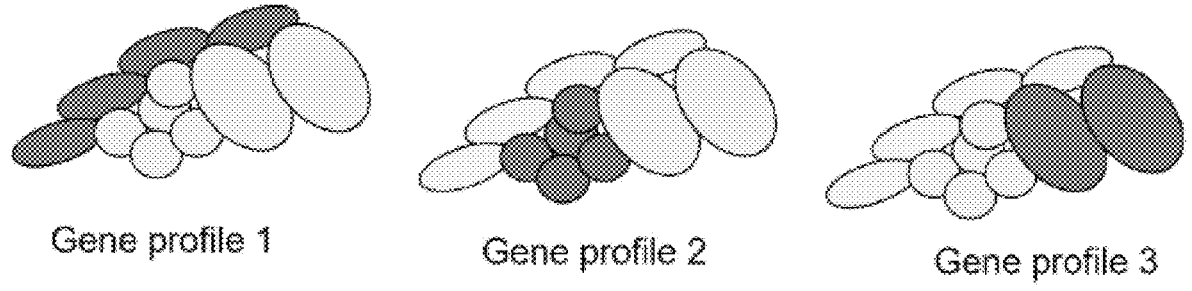
FIG. 6 depicts mapping of gene profiles to initial tissue locations.

FIG. 6 depicts spatial profiling of the cell following methods of the invention. Cell transcriptome information is associated with a grid position by the ADT barcode. Cell types, for example by transcription profile, can then be aligned to the spatial arrangement of cells.

In aspects of the invention, tissue indexing slides may be imaged directly be microscopy. This may advantageously allow for direct correlation of spatial transcriptomics with high resolution imaging. Additional staining antibodies may also be ADT labeled for CITE-seq assays as described in Stoeckius, 2017, Simultaneous epitope and transcriptome measurement in single cells, Nat Methods 14(9):865-868, incorporated by reference. Spatial indexing alone may be sufficient to assign localization of nuclei without further microscopy.

The array may utilize 2-axis indexing, rather than requiring individual barcodes for each spatial index spot. Each spot may comprise two labels, for example ADT labels, one each for X and Y axis. This is advantageous because it reduces the total number of required labels. Each labeled cell or nucleus would therefore be assigned two spatially specific barcodes.

In aspects of the invention, labels comprising spatially indexed primers may be direct printed onto tissue slices without the need for an array. Precision instruments and labeling reagents, for example stock ADT reagents may be applied at the site of printing. Labels may be spotted directly onto the array and the array lyophilized adhering labels to the surface of the array, for example the glass surface of a slide array. The labels may be formulated with excipients to promote uniform, rapid dissolution of the labels upon wetting of the array. Labels may be covalently linked to the array surface to stabilize spatial location. For example, siloxane chemistry may be used to prepare the array. The index nucleic acid moiety may also comprise a cleavable base or moiety to allow for controlled release of the label, for example through a disulfide bond or photocleavable bond. Label localization may be promoted by photopatterning the array to incorporate hydrophilic and hydrophobic patches. Labels would be localized to hydrophilic spots.

Gene Expression Profiling

Gene expression profiling is the measurement of the actual expression of genes. Gene expression profiling includes the identification of mRNA being expressed and the measurement of the quantity of that mRNA in the cell to measure the activity of the corresponding genes. While sequencing a genome provides information as to what the cell could possibly do, the expression profile provides information as to what the cell is actually doing at a point in time.

At any moment, generally each cell makes mRNA from only a fraction of the genes it carries. If a gene is used to produce mRNA, it is generally considered "on", otherwise "off". For example, cells may be modified by an RNA guide that is thought to produce an "on" switch in a gene, an RNA guide that is thought to produce as "off" switch in a gene, and an RNA guide that is thought to produce no change in the gene. The gene expression profile provides information as to what the changes made by the guide RNAs in DNA actually result in phenotypic changes in the mRNA expression in the cell. Gene expression profiling may also provide information as to the editing capacity of an RNA guide. For example, when multiple RNA guides targeting the same "on" switch are analyzed in parallel, the varying levels of gene expression changes may be used to analyze the activity of the guide.

Gene expression profiling is useful for analyzing genetic diseases with varying disease states, for example cancers, neurodegenerative diseases, neuropsychiatric disease, metabolic disorders, and cardiovascular disorders. Metabolic disorders may include type 2 diabetes and obesity. Cardio-vascular disorders may include atherosclerosis and hyper-tension. Neurological disorders may include Alzheimer's or Parkinson's. Cancers may include Hodgkin lymphoma, non-Hodgkin lymphoma, myelodysplastic syndromes, breast cancer, prostate cancer, melanoma, ovarian cancer, sarcoma, oral carcinoma, or a hepatocellular carcinoma.

Moreover, gene expression profiling can be useful for identifying the mechanisms of action of therapeutic inter-ventions, for example small molecule drugs.

Barcodes and Unique Molecular Identifiers

Barcodes specific to each PIP may be any group of nucleotides or oligonucleotide sequences that are distin-guishable from other barcodes within the group. A PIP encapsulating a template particle and a single cell provides to each nucleic acid molecule released from the single cell the same barcode from the group of barcodes. The barcodes provided by each PIP are unique to that PIP and distinguish-able from the barcodes provided to nucleic acid molecules by every other PIP. Once sequenced, by using the barcode sequence, the nucleic acid molecules can be traced back to the PIP and thereby to each single cell. Barcodes may be of any suitable length sufficient to distinguish the barcode from other barcodes. For example, a barcode may have a length of 4, 5, 6, 7, 8, 9, 10, 11, 12, 13, 14, 15, 16, 17, 18, 19, 20, 21, 22, 23, 24, 25 nucleotides, or more.

The barcodes unique to each PIP may be pre-defined, degenerate, and/or selected at random. Barcodes may be added to nucleic acid molecules by "tagging" the nucleic acid molecules with the barcode. Tagging may be performed using any known method for barcode addition, for example direct ligation of barcodes to one or more of the ends of each nucleic acid molecule. Nucleic acid molecules may, for example, be end repaired in order to allow for direct or blunt-ended ligation of the barcodes. Barcodes may also be added to nucleic acid molecules through first or second strand synthesis, for example using capture probes or prim-ers.

Unique molecular identifiers are a type of barcode that may be provided to nucleic acid molecules in a sample to make each nucleic acid molecule, together with its barcode, unique, or nearly unique. This is accomplished by adding, e.g. by ligation, one or more UMIs to each nucleic acid molecule such that it is unlikely that any two previously identical nucleic acid molecules, together with their UMIs, have the same sequence. By selecting an appropriate number of UMIs, every nucleic acid molecule in the sample, together with its UMI, will be unique or nearly unique. One strategy for doing so is to provide to a sample of nucleic acid molecules a number of UMIs in excess of the number of starting nucleic acid molecules in the sample. By doing so, each starting nucleic molecule will be provided with differ-ent UMIs, therefore making each molecule together with its UMIs unique. However, the number of UMIs provided may be as few as the number of identical nucleic acid molecules in the original sample. For example, where no more than six nucleic acid molecules in a sample are likely to be identical, as few as six different UMIs may be provided, regardless of the number of starting nucleic acid molecules.

UMIs are also advantageous in that they can be useful to correct for errors created during amplification, such as amplification bias or incorrect base pairing during amplifi-cation. For example, when using UMIs, because every nucleic acid molecule in a sample together with its UMI or UMIs is unique or nearly unique, after amplification and sequencing, molecules with identical sequences may be considered to refer to the same starting nucleic acid molecule, thereby reducing amplification bias. Methods for error correction using UMIs are described in Karlsson, 2016, Counting Molecules in cell-free DNA and single cells RNA, Thesis, Inst för medicinsk biokemi och biofysik, Stockholm Sweden (52 pages), incorporated by reference.

Template Particles

The template particles of the present disclosure may be prepared using any method known in the art. Generally, the template particles are prepared by combining hydrogel material, e.g., agarose, alginate, a polyethylene glycol (PEG), a polyacrylamide (PAA), Acrylate, Acrylamide/ bisacrylamide copolymer matrix, and combinations thereof. Following the formation of the template particles they are sized to the desired diameter for capturing and uniquely tagging cells. For example, sizing of the template particles may be done by microfluidic co-flow into an immiscible oil phase.

Template particles may vary in size. Variation may be limited, for example the diameter or largest dimension of the template particles may be such that at least 50% or more, e.g., 60% or more, 70% or more, 80% or more, 90% or more, 95% or more, or 99% or more of the template particles vary in diameter or largest dimension by less than a factor of 10, e.g., less than a factor of 5, less than a factor of 4, less than a factor of 3, less than a factor of 2, less than a factor of 1.5, less than a factor of 1.4, less than a factor of 1.3, less than a factor of 1.2, less than a factor of 1.1, less than a factor of 1.05, or less than a factor of 1.01.

Advantageously, the absorbency of the presently dis-closed template particles may be increased by storing them in a dehydrated condition prior to using them in the presently disclosed method for single cell analysis, with the general intention of shrinking their volume. Advantageously, shrink-ing template particles allows for control of the template particle shape and size for capturing cells and barcoding released nucleic acid molecules, for example with barcodes unique to each PIP. For example, dehydration of the tem-plate particles may be achieved by storing them in a high osmolarity buffer to promote shrinking (i.e. Polyethelene glycol). Alternatively, the template particles may be ethanol dehydrated. Shrinking may occur upon the application of an external stimulus, e.g., heat. For instance, the template particles may be encapsulated in a fluid by shearing, fol-lowed by the application of heat, causing the template particles to shrink in size. Some other examples of drying approaches include, but are not limited to, heating, drying under vacuum, freeze drying, and supercritical drying. The dried template particles may also be combined with a fluid, but still retain the shape and structure as independent, often spherical, gel particles. The dried template particles may be combined with an appropriate fluid, causing a portion of the fluid to be absorbed by the template particles. Porosity of the template particles may also vary, to allow at least one of a plurality of cells to be absorbed into the template particles when combined with the appropriate fluid. Any convenient fluid that allows for the desired absorption to be performed in the template particles may be useful for methods of the invention.

Template particles are advantageously tiny, generally spherical, particles. Template particles may be porous or nonporous. Template particles may also include microcom-partments or internal compartments which advantageously may contain additional components and/or reagents, for example, additional components and/or reagents that may be releasable into PIPs.

Template particles may include a polymer such as a hydrogel. Template particles generally range from about 0.1 to about 1000 μm in diameter or largest dimension. Template particles may have a diameter or largest dimension of about 1.0 μm to 1000 μm, inclusive, such as 1.0 μm to 750 μm, 1.0 μm to 500 μm, 1.0 μm to 250 μm, 1.0 μm to 200 μm, 1.0 μm to 150 μm 1.0 μm to 100 μm, 1.0 μm to 10 μm, or 1.0 μm to 5 μm, inclusive. Template particles may have a diameter or largest dimension of about 10 μm to about 200 μm, e.g., about 10 μm to about 150 μm, about 10 μm to about 125 μm, or about 10 μm to about 100 μm.

Cells analyzed by the present invention may include live cells obtained from, for example, a sample (tissue of bodily fluid) of a patient. The sample may include a fine needle aspirate, a biopsy, or a bodily fluid from the patient. Upon being isolated from the sample, the cells may be processed by, for example, generating a single cell suspension with an appropriate solution. Such solution will generally be a balanced salt solution, e.g. normal saline, PBS, HBSS (Hank's balanced salt solution), etc., and in certain instances supplemented with fetal calf serum or other naturally occurring factors, in conjunction with an acceptable buffer at low concentration, generally from 5-25 mM. Convenient buffers include HEPES, phosphate buffers, lactate buffers, etc. The separated cells can be collected in any appropriate medium that maintains the viability of the cells, usually having a cushion of serum at the bottom of the collection tube. Various media are commercially available and may be useful according to the nature of the cells, including dMEM, HBSS, DPBS, RPMI, IMDM (Iscove's medium), etc., frequently supplemented with fetal calf serum. Preferably, the cells are mammal cells, for example human cells.

The composition and nature of the template particles may vary depending on the single cell analysis being conducted. For instance, the template particles may be microgel particles that are micron-scale spheres of gel matrix. The microgels are composed of a hydrophilic polymer that is soluble in water, including alginate or agarose. Microgels may also be composed of a lipophilic microgel.

Template particles may also be a hydrogel, such as hydrogels from naturally derived materials, synthetically derived materials, and combinations thereof. Examples of hydrogels include, but are not limited to, collagen, hyaluronan, chitosan, fibrin, gelatin, alginate, agarose, chondroitin sulfate, polyacrylamide, polyethylene glycol (PEG), polyvinyl alcohol (PVA), acrylamide/bisacrylamide copolymer matrix, polyacrylamide/poly(acrylic acid) (PAA), hydroxyethyl methacrylate (HEMA), poly N-isopropylacrylamide (NIPAM), and polyanhydrides, poly(propylene fumarate) (PPF).

Template particles may further advantageously comprise materials which provide the template particles with a positive surface charge, or an increased positive surface charge. Such materials may be without limitation poly-lysine or Polyethyleneimine, or combinations thereof. This may increase the chances of association between the template particle and, for example, a cell which generally have a mostly negatively charged membrane.

Other strategies aimed to increase the chances of template particle-cell association include creation of a specific template particle geometry. For example, the template particles may have a general spherical shape but the shape may contain features such as flat surfaces, craters, grooves, protrusions, and other irregularities in the spherical shape.

Any one of the above described strategies and methods, or combinations thereof may be useful in the practice of the presently disclosed template particles and method for single cell analysis thereof. Methods for generation of template particles, and template particles-based encapsulations, were described in International Patent Publication WO 2019/139650, which is incorporated herein by reference.

To increase the chances of generating partitions that contain one template particle and one single cell, the template particles and cells may be combined at a ratio wherein there are more template particles than cells. For example, the ratio of template particles to cells combined in a mixture as described above may be in a range of 5:1 to 1,000:1, respectively. The template particles and cells may also be combined at a ratio of 10:1, 100:1, or 1000:1, respectively.

To generate a monodisperse emulsion, a step of shearing the second mixture provided by combining a first mixture comprising template particles and cells with a second fluid immiscible with the first mixture. Any suitable method may apply a sufficient shear force to the second mixture. For example, the second mixture may be sheared by flowing the second mixture through a pipette tip. Other methods include, but are not limited to, shaking the second mixture with a homogenizer (e.g., vortexer), or shaking the second mixture with a bead beater. Vortexing may be performed for example for 30 seconds, or in the range of 30 seconds to 5 minutes. The application of a sufficient shear force breaks the second mixture into partitions that encapsulate one of a plurality of template particles.

Generating the template particle-based partitions may involve shearing two liquid phases. For example, the mixture may be the aqueous phase and comprise reagents selected from, for example, buffers, salts, lytic enzymes (e.g. proteinase k) and/or other lytic reagents (e. g. Triton X-100, Tween-20, IGEPAL, bm 135, or combinations thereof), nucleic acid synthesis reagents e.g. nucleic acid amplification reagents, or combinations thereof. The fluid may be the continuous phase and may be an immiscible oil such as fluorocarbon oil, a silicone oil, or a hydrocarbon oil, or a combination thereof. The fluid may advantageously comprise reagents such as surfactants (e.g. octylphenol ethoxylate and/or octylphenoxypolyethoxyethanol), reducing agents (e.g. DTT, beta mercaptoethanol, or combinations thereof).

In practicing methods as described herein, the composition and nature of the partitions, e.g., single-emulsion and multiple-emulsion partitions, may vary. Advantageously, a surfactant may be useful to stabilize the partitions. The PIPs described herein may be prepared as emulsions, e.g., as an aqueous phase fluid dispersed in an immiscible phase carrier fluid (e.g., a fluorocarbon oil, silicone oil, or a hydrocarbon oil) or vice versa. Accordingly, a partition may involve a surfactant stabilized emulsion, e.g., a surfactant stabilized single emulsion or a surfactant stabilized double emulsion. Any convenient surfactant that allows for the desired reactions to be performed in the partitions may be useful. In other aspects, PIPs are not stabilized by surfactants.

Template particles useful in the present invention may further comprise a cell capture moiety. The cell capture moiety acts to capture specific cells, for example, specific types of cells. The capture moiety may comprise an Acrylate-terminated hydrocarbon linker with biotin termination. The capture moiety may be attached to a target-specific capture element, for example aptamers and/or antibodies. Examples of capture moieties and methods thereof are disclosed in PCT application no. PCT/US2019/053426, incorporated herein by reference.

Reverse Transcription, Amplification, and Sequencing

Methods of the invention generally relate to analysis and sequencing of gene transcripts from single cells modified by RNA guides in genomic areas of interest, for example oncogenes. PCR amplification of products derived from nucleic acid molecules released by single cells can be useful to determine a gene expression profile for a cell for preselected gene mutations, e.g., mutations associated with cancer. For example, identification of a gene or mutation of interest may provide information that the cell from which the nucleic acid molecule was released is expressing gene transcripts associated with cancer as a result of the genomic modification resulting from the RNA guide. Because each nucleic acid molecule is tagged with a barcode unique to the PIP and single cell from which it was released, any gene transcript can be traced back to the PIP and single cell, thereby allowing for the identification of an RNA guide and genotypic modification created by the RNA guide.

For RNA or mRNA sequencing, sequencing may first comprise the step of preparing a cDNA library from barcoded RNA, for example through reverse transcription, and sequencing the cDNA. cDNA sequencing may advantageously allow for the quantification of gene expression within the single cell, and can be useful to identify characteristics of the single cell to, for example, make a diagnosis, prognosis, or determine drug effectiveness. Reverse transcription of cDNA molecules from RNA can be performed both within the PIP or after barcoded RNA molecules have been released from each PIP.

Reverse transcription may be performed using without limitation dNTPs (mix of the nucleotides dATP, dCTP, dGTP and dTTP), buffer/s, detergent/s, or solvent/s, as required, and suitable enzyme such as polymerase or reverse transcriptase. The polymerase used may be a DNA polymerase, and may be selected from Taq DNA polymerase, Phusion polymerase (as provided by Thermo Fisher Scientific, Waltham, Massachusetts), or Q5 polymerase. Nucleic acid amplification reagents are commercially available, and may be purchased from, for example, New England Biolabs, Ipswich, MA, USA. The reverse transcriptase used in the presently disclosed targeted library preparation method may be for example, maxima reverse transcriptase. In some embodiments, the general parameters of the reverse transcription reaction comprise an incubation of about 15 minutes at 25 degrees and a subsequent incubation of about 90 minutes at 52 degrees.

Reverse transcription may be performed by oligos that have a free, 3' poly-T region. The 3' portions of the cDNA capture oligos may include gene-specific sequences or oligomers, for example capture primers to reverse transcribe RNA guides comprising a capture sequence. The oligomers may be random or "not-so-random" (NSR) oligomers (NS-ROs), such as random hexamers or NSR hexamers. The oligos may include one or more handles such as primer binding sequences cognate to PCR primers that are used in the amplifying step or the sequences of NGS sequencing adaptors. The reverse transcription primers may include template switching oligos (TSOs), which may include poly-G sequences that hybridize to and capture poly-C segments added during reverse transcription.

Reverse transcription of non-polyadenylated RNA may comprise use of a capture sequence and a capture primer or probe. Primer sequences may comprise a binding site, for example a primer sequence that would be expected to hybridize to a complementary sequence, if present, on any nucleic acid molecule released from a cell and provide an initiation site for a reaction. The primer sequence may also be a "universal" primer sequence, i.e. a sequence that is complementary to nucleotide sequences that are very common for a particular set of nucleic acid fragments. Primer sequences may be P5 and P7 primers as provided by Illumina, Inc., San Diego, California. The primer sequence may also allow a capture probe to bind to a solid support, such as a template particle.

Reverse transcription can also be useful for adding a barcode unique to the PIP or a UMI, or both to cDNA. This process may comprise hybridizing the reverse transcription primer to the probe followed by a reverse transcription reaction. The complement of a nucleic acid when aligned need not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

Nucleic acid molecules may advantageously be amplified prior to sequencing. Amplification may comprise methods for creating copies of nucleic acids by using thermal cycling to expose reactants to repeated cycles of heating and cooling, and to permit different temperature-dependent reactions (e.g. by Polymerase chain reaction (PCR). Any suitable PCR method known in the art may be used in connection with the presently described methods. Non limiting examples of PCR reactions include real-time PCR, nested PCR, multiplex PCR, quantitative PCR, or touchdown PCR. Notably, each amplified copy of the nucleic acid molecule will comprise the barcode unique to a PIP for identifying the PIP and cell from which the nucleic acid molecule was released and a UMI. Methods for amplification many include whole genome amplification.

Sequencing nucleic acid molecules may be performed by methods known in the art. For example, see, generally, Quail, et al., 2012, A tale of three next generation sequencing platforms: comparison of Ion Torrent, Pacific Biosciences and IlluminaMiSeq sequencers, BMC Genomics 13:341. Nucleic acid molecule sequencing techniques include classic dideoxy sequencing reactions (Sanger method) using labeled terminators or primers and gel separation in slab or capillary, or preferably, next generation sequencing methods. For example, sequencing may be performed according to technologies described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232, 656, 7,598,035, 6,306,597, 6,210,891, 6,828,100, 6,833,246, and 6,911,345, each incorporated by reference.

The conventional pipeline for processing sequencing data includes generating FASTQ-format files that contain reads sequenced from a next generation sequencing platform, aligning these reads to an annotated reference genome, and quantifying expression of genes. These steps are routinely performed using known computer algorithms, which a person skilled in the art will recognize can be used for executing steps of the present invention. For example, see Kukurba, Cold Spring Harb Protoc, 2015 (11):951-969, incorporated by reference.

Tubes for Generating PIPs

As described above, tubes may be selected based on the volume of sample from which cells need to be separated and/or based on the number of cells to be separated. For example, the tube may be a single large tube, such as a conical centrifuge tube, such as a Falcon® as sold by Corning Inc., Corning, New York, for example a tube with a volume of less than 40 mL. Such tubes may be advantageous where the number of cells to be analyzed is between 100,000 and 1 million cells or greater than 1 million cells. This method is useful when analyzing cells for targeted coverage of heterogeneous cell types and exploring pathways in complex tissues, for example in cancer detection in mixed cell populations.

The tubes may also be wells, such as standard 96 sample well kit. The well may be part of a microplate with multiple wells each using a tube. The microplate may comprise any number of wells as desired, for example 6-1536 wells. Advantageously, the microplate may comprise 96 wells. Wells may be advantageous where the number of cells to be analyzed is about 100 cells. This method is useful when deep profiling homogenous cells under different conditions, such as early cancer detection in a tumor site.

The tubes may also be centrifuge, microcentrifuge, or PCR tubes, such as those sold EPPENDORF of Hamburg, Germany. Such tubes, for example, may be between 0.1 and 6 mL and are advantageous where the number of cells to be analyzed is about 10,000 cells. This method is useful when deep profiling heterogeneous cell populations, for example in early cancer detection in mixed cell populations.

As described above, because cells are encapsulated in PIPs simultaneously, methods of the present invention are easily scaled for the analysis of any number of cells. For example, tubes may be selected to analyze at least 1 million cells, at least 2 million cells, at least 10 million, at least than 100 million cells, or 200 million cells of greater. Additionally, because cells are encapsulated simultaneously, for any tubes and any number of cells sample preparation for sequencing may be completed within one day, and can be completed within three hours. Moreover, preparation of samples within each tube may be completed in as little time as about 5 minutes or about 2 minutes.

Primers and/or reagents may be added to the PIPS after formation of the PIPs in the tube. Primers and/or reagents may be added in one step, or in more than one step. For instance, the primers may be added in two or more steps, three or more steps, four or more steps, or five or more steps. Regardless of whether the primers are added in one step or in more than one step, they may be added after the addition of a lysing agent, prior to the addition of a lysing agent, or concomitantly with the addition of a lysing agent. When added before or after the addition of a lysing agent, PCR primers may be added in a separate step from the addition of a lysing agent.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for gene expression profiling, the method comprising:
    incubating a tissue sample on an array comprising a plurality of labels having binding specificity for a cellular protein and having a nucleic acid index identifying the location of the label on the array, wherein the labels are lyophilized and released upon wetting of the array;
    disaggregating a plurality of cells from the tissue sample;
    combining the disaggregated plurality of cells with template particles; and
    generating a plurality of uniform partitions substantially instantly that encapsulate a single one of the template particles and a single one of the disaggregated cells to form pre-templated instant partitions (PIPs); and
    releasing in each PIP nucleic acid molecules and proteins from the disaggregated cells, including proteins bound by a label from the array.

2. The method of claim 1, wherein the labels comprise a DNA-conjugated antibody or fragment, a DNA-conjugated aptamer, or a DNA-conjugated lipid.

3. The method of claim 1, wherein the step of releasing nucleic acid molecules from the cells comprises releasing RNA molecules.

4. The method of claim 3, wherein each of the nucleic acid molecules and labels released from a cell in each PIP is provided a nucleic acid barcode unique to the PIP.

5. The method of claim 4, wherein each of the nucleic acid molecules is provided with a unique molecular barcode.

6. The method of claim 5, wherein the step of providing a nucleic acid barcode unique to the PIP and a unique molecular identifier comprises the step of reverse transcribing RNA molecules to form cDNA complements comprising the unique molecular identifier and barcode unique to the PIP.

7. The method of claim 6, further comprising the step of sequencing the cDNA complements to generate sequence reads associated with each RNA molecule.

8. The method of claim 7, further comprising the step of associating each label from a PIP with each sequence read associated with an RNA molecule from the same PIP to generate a set of sequence reads for each label.

9. The method of claim 1, wherein the step of incubating the tissue sample comprises:
    i) permeabilizing the tissue sample;
    ii) staining the tissue sample; and/or
    iii) imaging the tissue sample.

10. The method of claim 1, wherein the labels have specificity for a nuclear envelope cell protein, disaggregated proteins, or nuclear proteins.

11. The method of claim 1, wherein each index identifies at least the X and/or Y coordinates of the label on the array.

12. The method of claim 11, wherein each location on the array comprises at least two labels together identifying the X and Y coordinates of the location on the array.

13. The method of claim 1, wherein the array is a glass array.

14. The method of claim 13, wherein the labels are spotted onto the glass array.

15. The method of claim 13, wherein the labels are covalently bonded to the glass array.

16. The method of claim 14, wherein the labels are covalently bonded to the glass array by siloxane chemistry.

17. The method of claim 16, wherein the labels are covalently bonded to the glass array by their index.

18. The method of claim 17, wherein the index comprises a moiety for controlled release of label.

19. The method of claim 1, wherein:

the step of combining the template particles with the plurality of disaggregated cells comprises combining the particles and cells in a first fluid and adding a second fluid to the first fluid, wherein the first fluid and second fluid are immiscible;

the step of generating a plurality of uniform partitions near-instantly comprises: agitating the fluids to generate the PIPs that contain a single one of the template particles and a single one of the disaggregated cells; and/or the step of releasing in each PIP nucleic acid molecules from the cells comprises: lysing each of the single cells contained within the PIPs.

20. The method claim 19, wherein the step of combining cells and template particles and the step of generating a plurality of uniform partitions near-instantly are performed in a tube, wherein the tube is a centrifuge, microcentrifuge, or polymerase chain reaction (PCR) tube.

21. The method of claim 20, wherein the step of generating in the tube a plurality of uniform partitions near-instantly that encapsulate a single one of the template particles and a single one of the cells comprises generating a plurality of partitions that encapsulate a single one of the template particles and do not encapsulate a cell.

* * * * *